United States Patent [19]

London

[11] Patent Number: 4,988,062

[45] Date of Patent: Jan. 29, 1991

[54] APPARATUS, SYSTEM AND METHOD FOR ORGANIZING AND MAINTAINING A PLURALITY OF MEDICAL CATHETERS AND THE LIKE

[76] Inventor: Robert A. London, 1252 Wellington Ter., Maitland, Fla. 32751

[21] Appl. No.: 166,104

[22] Filed: Mar. 10, 1988

[51] Int. Cl.[5] .......................... A61M 5/14

[52] U.S. Cl. .......................... 248/68.1; 248/282; 248/289.1; 28/DIG. 26; 604/80

[58] Field of Search .................... 248/68.1, 282, 289.1, 248/122, 65, 74.1, 118, 49; 604/80, 81, 174, 905, 179, 82, 83, 173; 128/DIG. 26; 269/328; 5/508; 24/16 PB

[56] References Cited

U.S. PATENT DOCUMENTS

| | | | |
|---|---|---|---|
| 2,455,757 | 12/1948 | Graybeal | 269/328 |
| 2,710,004 | 6/1955 | Stamper | 604/80 |
| 3,091,287 | 5/1963 | Willoughby | 248/289.1 |
| 3,625,210 | 12/1971 | Mikkelson | 604/174 |
| 3,995,846 | 12/1976 | Frick | 269/328 |
| 4,019,727 | 4/1977 | Martin | 269/328 |
| 4,025,015 | 5/1977 | Kolic | 128/DIG. 26 X |
| 4,127,120 | 11/1978 | Applegate | 269/328 |
| 4,141,524 | 2/1979 | Corvese, Jr. | 248/231.4 X |
| 4,226,036 | 10/1980 | Krug | 24/16 PBX |
| 4,239,200 | 12/1980 | Sarafian | 269/328 |
| 4,553,724 | 11/1985 | St.-Amand | 248/68.1 |
| 4,617,012 | 10/1986 | Vaillancourt | 604/905 X |
| 4,619,640 | 10/1986 | Potolsky et al. | 604/905 X |
| 4,692,144 | 9/1987 | Carpenter | 604/86 X |
| 4,706,368 | 11/1987 | Crissman | 248/122 X |
| 4,720,881 | 1/1988 | Meyers | 5/508 X |
| 4,733,661 | 3/1988 | Palestrant | 128/DIG. 26 |
| 4,795,429 | 1/1989 | Feldstein | 604/82 X |

*Primary Examiner*—Alvin C. Chin-Shue

*Attorney, Agent, or Firm*—Duckworth, Allen, Dyer & Doppelt

[57] ABSTRACT

An apparatus, system and method for organizing and maintaining a plurality of catheters, valves, intravenous and monitoring lines for patient care includes a member having a surface dimensioned to receive a patient, and with at least one wing rotatably coupled to the member. The wing has a manifold at its distal extremity for receiving the catheters, intravenous and monitoring lines in a relatively fixed relation with respect to the patient during rotation of the wing. The wing is rotatable into numerous positions between a first position lateral to the sides of the member into a second position generally parallel to the member. An identifying sleeve at the opposite ends of each catheter or line further facilitates organization and identification.

30 Claims, 4 Drawing Sheets

FIG. 1
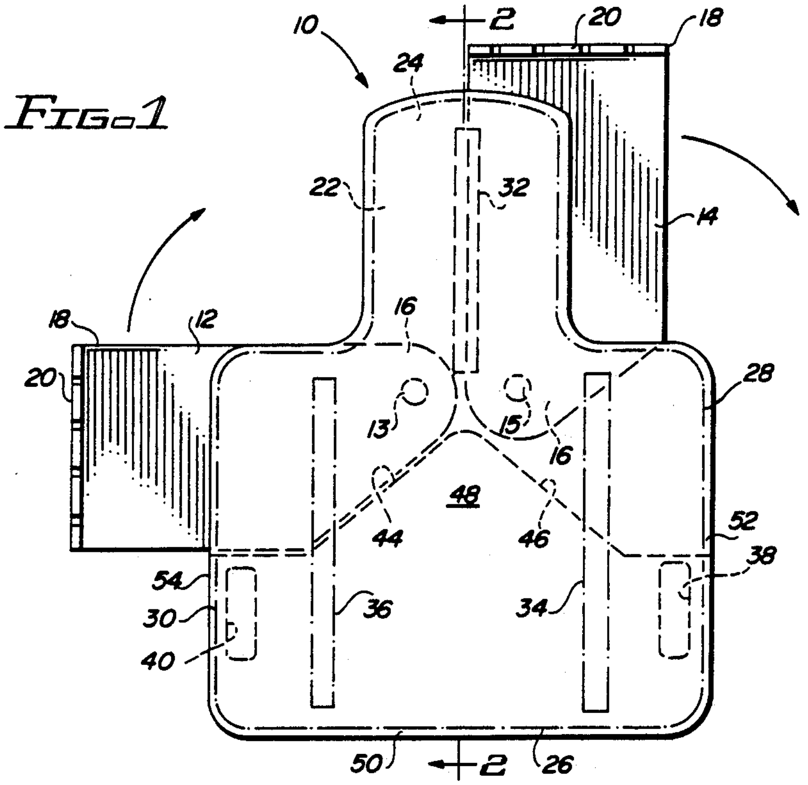
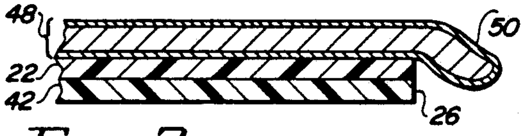
FIG. 2
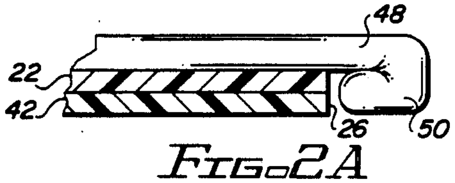
FIG. 2A
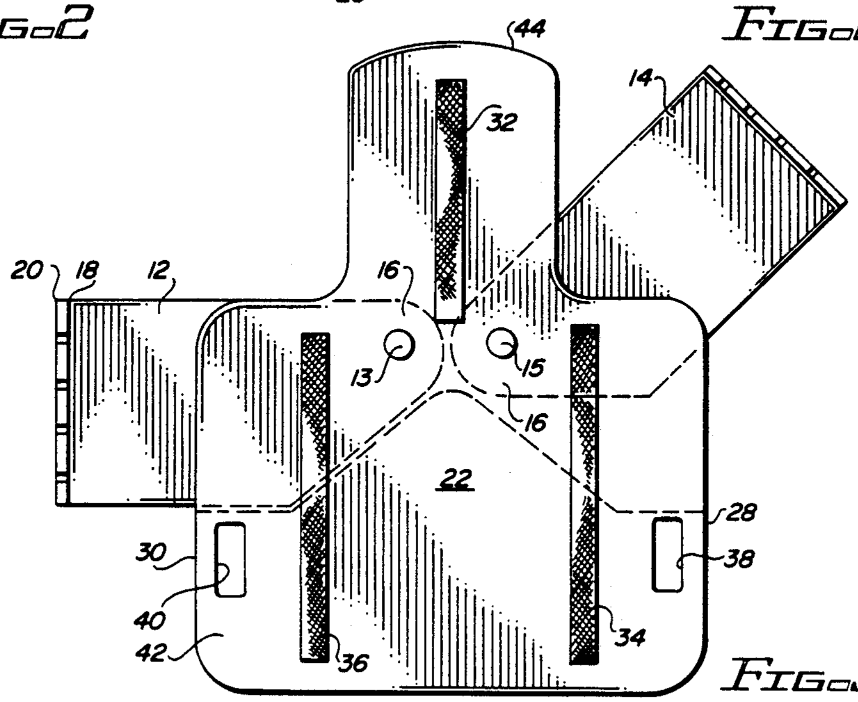
FIG. 3

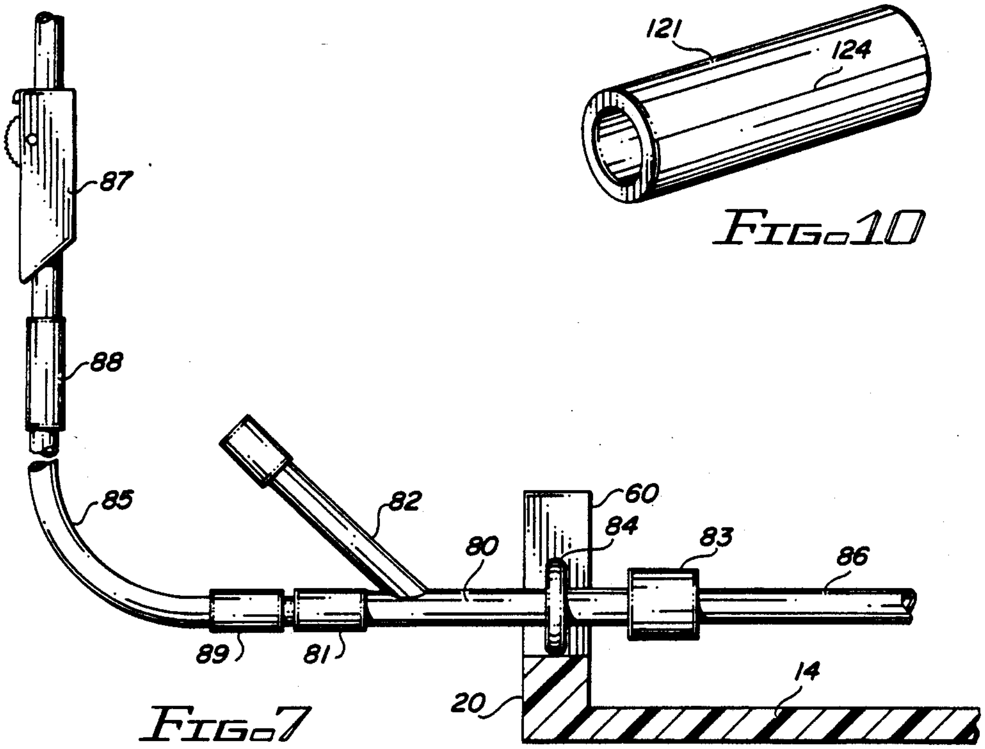
FIG. 10
FIG. 7
FIG. 8
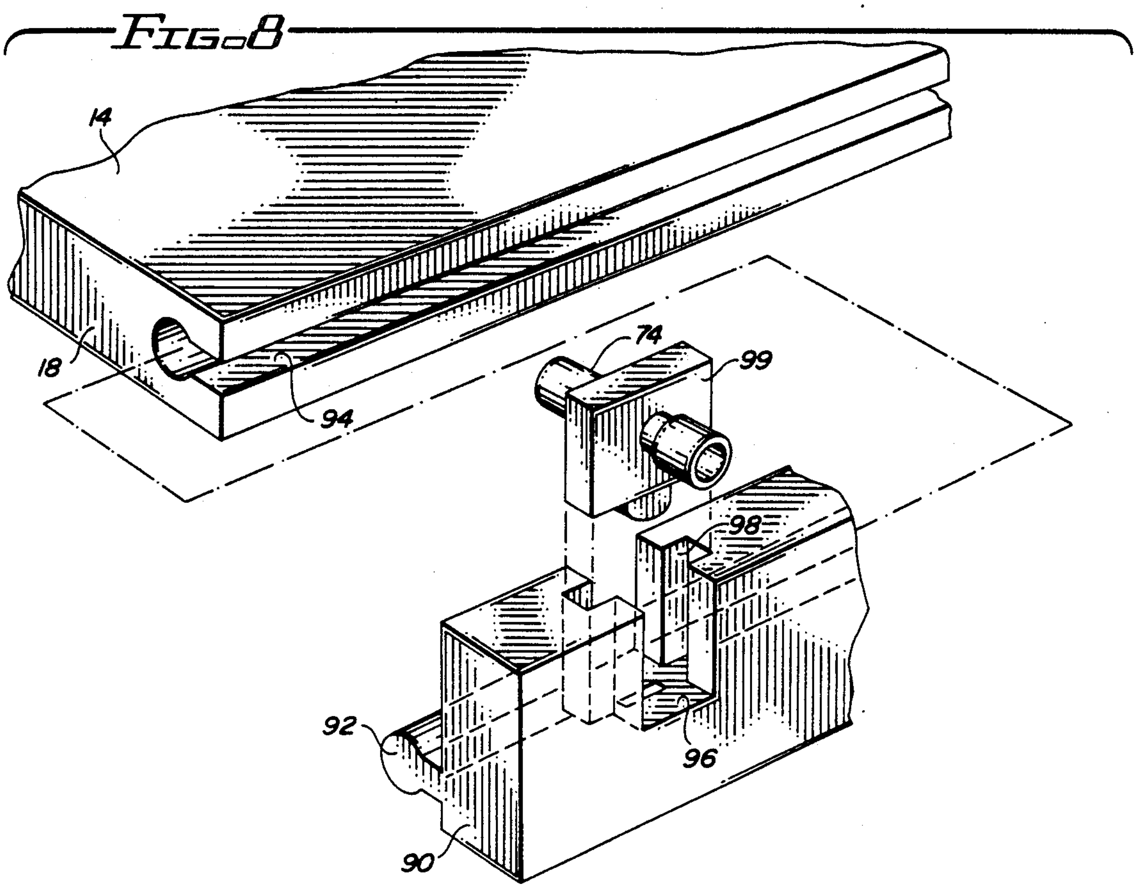

APPARATUS, SYSTEM AND METHOD FOR ORGANIZING AND MAINTAINING A PLURALITY OF MEDICAL CATHETERS AND THE LIKE

BACKGROUND OF THE INVENTION

1. Field of the Invention.

The present invention relates generally to medical devices, apparatus and methods, and specifically relates to techniques for identifying and organizing a plurality of catheters, intravenous lines and the like in preparation for and during patient transport as well before, during and after surgical and medical procedures, and thereafter maintaining those catheters and lines in an organized fashion.

2. Description of the Prior Art.

During the course of complex surgical and medical procedures, the patient is often infused simultaneously with a plurality of medications and fluids. Those medications and fluids are fed into the patient's body through catheters, intravenous and fluid lines and the like. Additionally, catheters are frequently utilized to monitor body functions, such as intra-cardiac, arterial and venous pressures. Many of these catheters, fluid lines and monitoring lines are put in place in the patient's body prior to the patient being transported. Frequently, when the patient is being transported, these catheters and lines have a tendency to become severely entangled, greatly compromising the ability of the attending physicians (such as anesthesiologist) to monitor the medications being infused, to give additional medications and/or to monitor body functions. This problem of confusing lines and catheters entering the patient's body is exacerbated under emergency conditions. A further difficulty is stress on the catheters and lines, causing them to become disconnected. These difficulties increase the risk of patient injury by either infusing medicine or blood at the wrong entry site, or by failing to infuse needed medications.

An example of such difficulties under emergency conditions frequently occurs during the administration of the well known percutaneous transluminal coronary artery angioplasty (PTCA) procedure, when it is determined that the patient will require emergency open heart surgery. During the PTCA procedure, numerous catheters and intravenous lines are already in place; if the patient requires emergency open heart surgery, then numerous additional catheters and intravenous lines are required as well.

Once in the operating room, the numerous catheters, intravenous and monitoring lines must be placed in such a way as to not cause stress on the entry site of each line, but nevertheless permit easy access to the infusion catheters and monitoring lines by the anesthesiologist, as well as access to the patient by the surgeon and operating team.

These problems described above are present with the need for non-emergent as well as emergent transport of patients whenever numerous pressure and intravenous catheters exists. Examples include the transport of these patients from one part of the hospital to another; or intensive care unit or cardiac care unit to X-ray for diagnostic tests or the operating room for surgery; or from the emergency room. Similar problems occur with intra hospital transport of such patients (via air helicopter/airplane; or ambulance).

SUMMARY OF THE INVENTION

The present invention is directed to an apparatus, system and method for identifying, organizing and maintaining a plurality of catheters, intravenous lines, monitoring lines and the like before and in preparation for patient transport, and before, during and after surgical and medical procedures in order to alleviate the difficulties noted above and reduce the risk to the patient, especially under emergency conditions. To this end, a support member having a surface dimensioned to receive a patient thereon is provided, the support member having at least one wing movably coupled to the member and further including means for receiving and holding a plurality of catheters, intravenous and monitoring lines and the like in a fixed relation to the patient during movement of the wing, with the wing preferably lying in and rotatable in a plane which is generally parallel to the plane of the surface upon which the patient rests. opposing ends and first and second opposing sides extending between the ends, and is adapted to receive the patient's head at the first end with the patient's torso extending along the member generally parallel with the sides. The wing is rotatable through an arc between numerous positions between a first extreme position generally lateral to one of the sides and a second extreme position generally parallel to the sides. The wing includes a manifold at its distal extremity to hold the various catheters and lines entering the patient.

In use, the wing may be rotated into a variety of selectable positions between the first and second extreme positions as may be required during pre-op, patient transport, operative or post-op patient care phases, or as may be dictated by the particular needs of the paramedic nurse, anesthesiologist, surgeon or ICU team.

In a preferred embodiment, the support member includes a second wing rotatably positioned on the opposing side from the first wing, and likewise includes a manifold at the distal extremity thereof for maintaining additional catheters and the like in the desired fixed relationship with the patient's body.

In order to provide patient comfort and to protect the support member during medical procedure, a padded cover is releasably attached to the upper surface of the member and is dimensioned to fit over the surface and extend beyond its extremities. The pad is suitably attached to the surface by means of a conventional hook and loop fabric fastener.

The wings and the pivot to which the wings are attached to the member have sufficient strength to permit lifting of the patient. Further, the pivot has a sufficient degree of friction to require some degree of pressure when the wings are being rotated between the extreme first and second positions, so that the wings do not inadvertently rotate out of the selected position. It is also desired that the wings be provided with a stop to preclude rotation toward to caudal (lower) end of the member.

The manifold for fixing the catheters and other lines to the distal end of each wing may take several forms. In its simplest form, the manifold consists of an upstanding plate having slots or grooves for permitting the catheters and lines to be frictionally engaged therein. The slots are also designed to receive one way valves and injection ports which are useful in some surgical and medical procedures. In use, the catheters, monitoring lines and valves may be moved from one slot to another in the same manifold, or alternatively moved to the other manifold. The upstanding plate may take the form of a disposable unit releasably attachable to the distal end of the wing so as to permit flexibility between different types of operating procedures.

Further in accord with another aspect of this invention, a pair of identification tags or sleeves are provided for each catheter or monitoring line, with one of the identifying tags or sleeves being fitted to the catheter or line near the corresponding injection port at the manifold slot and the other being attached to the catheter adjacent the IV flow clamp or medicine pump, pressure gauge or other device coupled to the catheter or line. In this way, the catheter or line remains correctly identified during the medical procedure.

DESCRIPTION OF THE DRAWING

FIG. 1 is a top plan view of the apparatus of the present invention, showing the pad placed over the support member, with the support member and its various parts (including the wings) illustrated by dotted lines.

FIGS. 2(*a*) and (*b*) are cross sections of the caudal (lower) extremity of the pad—member combination shown in FIG. 1.

FIG. 3 is a top plan view of the apparatus shown in FIG. 1 with the pad removed.

FIG. 5 is a perspective view of a portion of one wing of the apparatus shown in FIG. 1, illustrating one embodiment of a manifold for engaging the catheters, lines and the like.

FIG. 7 illustrates a one-way valve and manifold combination in accordance with the present invention.

FIG. 8 is a third embodiment of a manifold in accordance with the present invention.

FIG. 10 illustrates an identification sleeve of the present invention.

DESCRIPTION OF THE PREFERRED EMBODIMENT

Figure 4:
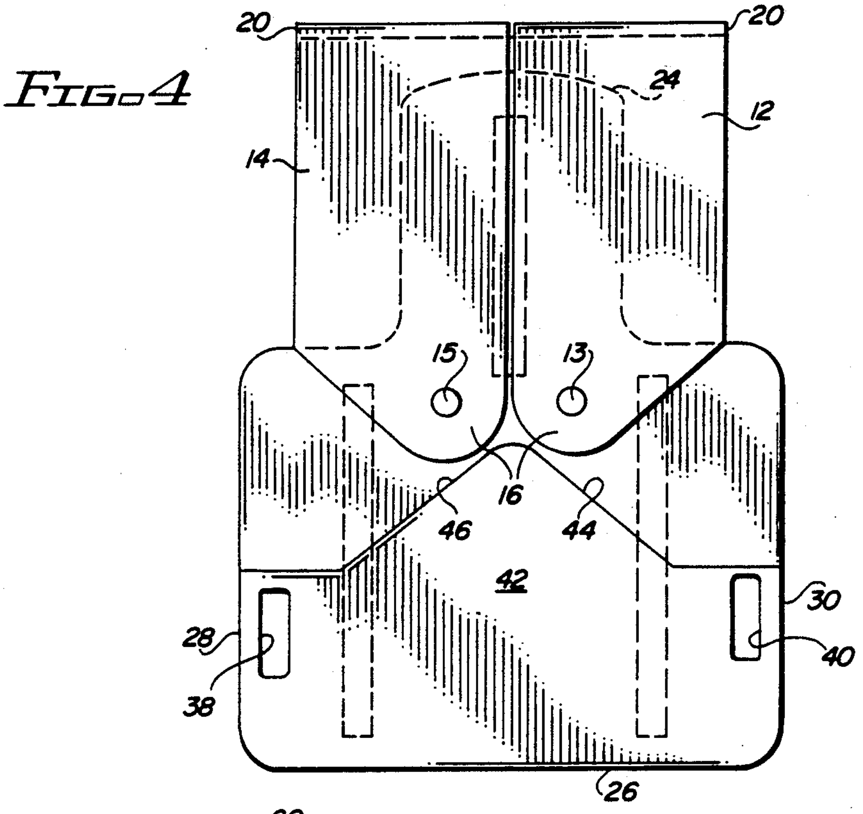
FIG. 4 is a bottom plan view of the member shown in FIG. 3, with the wings rotated to the second extreme position.

A preferred embodiment of the present invention will now be described with reference to FIGS. 1–4.

Referring first to FIG. 1, the apparatus 10 of the present invention is designed for identifying, organizing and maintaining a plurality of catheters (such as IV, medication and pressure lines) before and during patient transport, and before, during and after surgical and medical procedures. To that end, the apparatus 10 includes a pair of rotatable wings 12, 14 each of which has a proximal end 16 respectively pivoted about a corresponding pivot axis 13, 15 and further including a distal end 18. Each wing 12, 14 includes a manifold 20 at the distal end 18 for purposes of fixing the numerous catheters and pressure lines which are required to be utilized during patient care or transport, and in complex medical and surgical procedures, and to further hold those catheters in a fixed position relative to the patient's body when being rotated about the respective pivot axis 13, 15. In FIG. 1, one of the wings 12 is shown in a first extreme position extending laterally from one side of the apparatus 10 as is more fully described below. The other wing in FIG. 1 is shown rotated to a second extreme position generally out of the way of a patient resting upon the upper surface of the apparatus 10 (and with the head of the patient positioned at the upper extremity thereof). It will thus be understood that the rotation of the wings 12, 14 may be made to a variety of selected positions between the first and second extreme positions.

Now referring to FIGS. 1–4, the apparatus 10 includes a support member 22 consisting of a sheet which is preferably electrically non-conductive, fluoroscopically transparent, and has sufficient strength to support a patient when being moved from bed to gurney or when the patient is subjected to CPR or closed chest compression during emergencies. By way of example, LEXAN sheet is suitable for use as the member 22. The support member 22 includes upper and lower ends 24, 26 respectively and opposing sides 28 and 30 extending between its two ends. The first end 24 is adapted to support the patient's head, with the patient's torso extending across the support member 22 and generally parallel with the sides 28, 30. Suitably, the support member is sufficiently long so that the lower end 26 passes underneath the patient's lower back, although the support may be longer if desired.

To provide patient comfort and to protect the support member 22 during patient transport and the surgical and medical procedures, a cushioned pad 48 is releasably fastened to the upper surface of the support member 22 via fabric hook and loop fasteners 32, 34 and 36. The pad 48 at its lowermost extremity includes an overlapping portion 50 which extends substantially over the lower end 26 of the support member 22, in order to avoid pressure sores for the patient during and after surgical procedures (note two embodiments of FIGS. 2(*a*) and (*b*)). Likewise, the pad 48 has overlapping side portions 52 and 54 which respectively overlap the sides 28 and 30 of the support member 22 (note FIG. 1). The lower end 26 may also be tapered.

Referring specifically to FIGS. 3 and 4, a back plate 42 of fluoroscopically transparent material is attached with or formed as a part of the support member 22 and has edge surfaces 44 and 46 acting as stops against the rotation of the respective wings 12 and 14 (note FIG. 3). Lifting handles 38 and 40 are provided along sides 52 and 54 to facilitate the lifting of the patient while resting on the pad 48 and supported by the member 22.

The various embodiments of manifolds useful with the apparatus 10 will now be described with reference to FIGS. 5–8.

Figure 5:
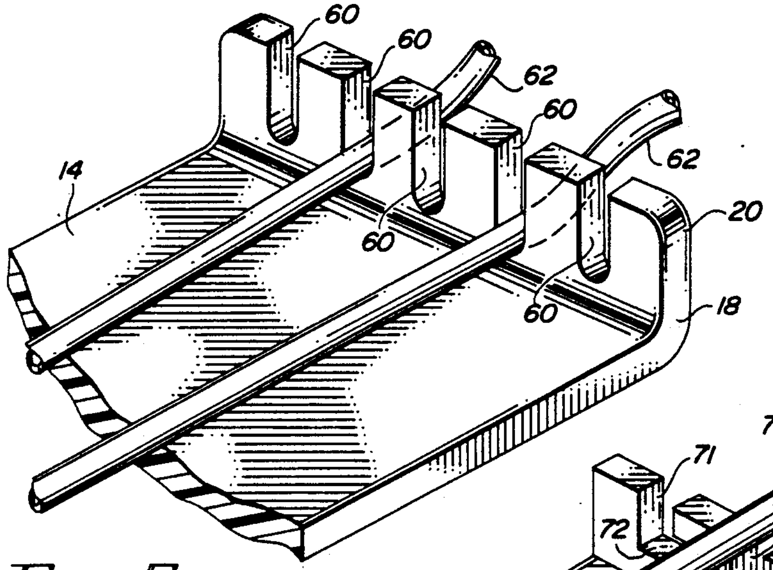
Figure 6:
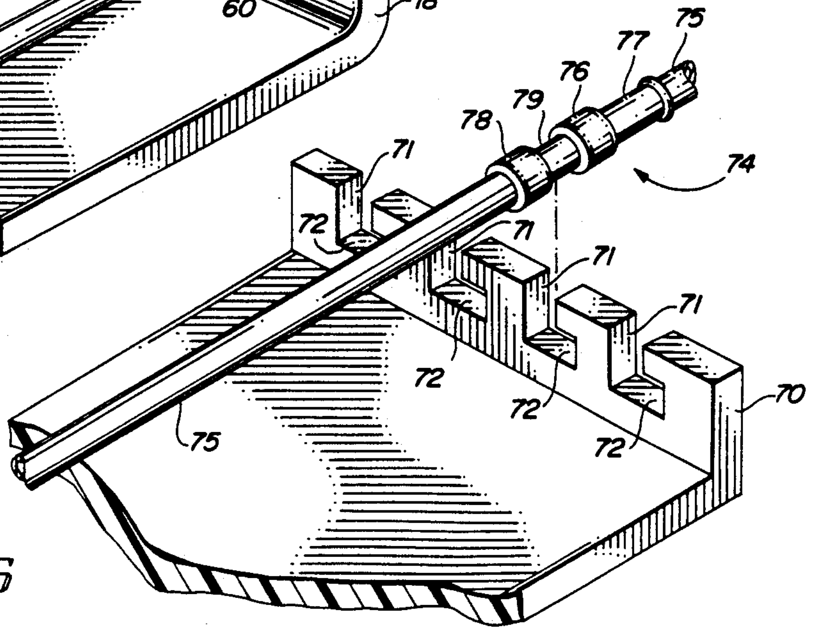
FIG. 6 is a perspective view of another embodiment of a catheter manifold in accordance with the present invention.

Noting FIG. 5, the wing 14 may include an integral, upstanding plate 20 having vertical grooves 60 into which fit the one way valves and the pressure lines (such as pressure lines 62). In the embodiment of FIG. 6, there is provided an upstanding plate 70 attached at the distal end of the wing 14, with vertical grooves 71 and horizontal slots 72 in the plate 70. The grooves and slots 71, 72 are adapted to receive a one way valve 74, consisting of a valve piece 76 and female and male connectors 77 and 78. Section 79 between the male member 78 and the one way valve 74 is adapted to fit into the slot and groove arrangement 72, 71 (or, the groove 60 in FIG. 5). A catheter 75 may then be attached to the respective male and female member 77, 78 to provide fluid flow through the one way valve 76, to insure that there is no flow in a reverse direction. Valves of this type also allow the rapid and facile exchange of various IV tubes without back flow and possible contamination.

Figure 9:
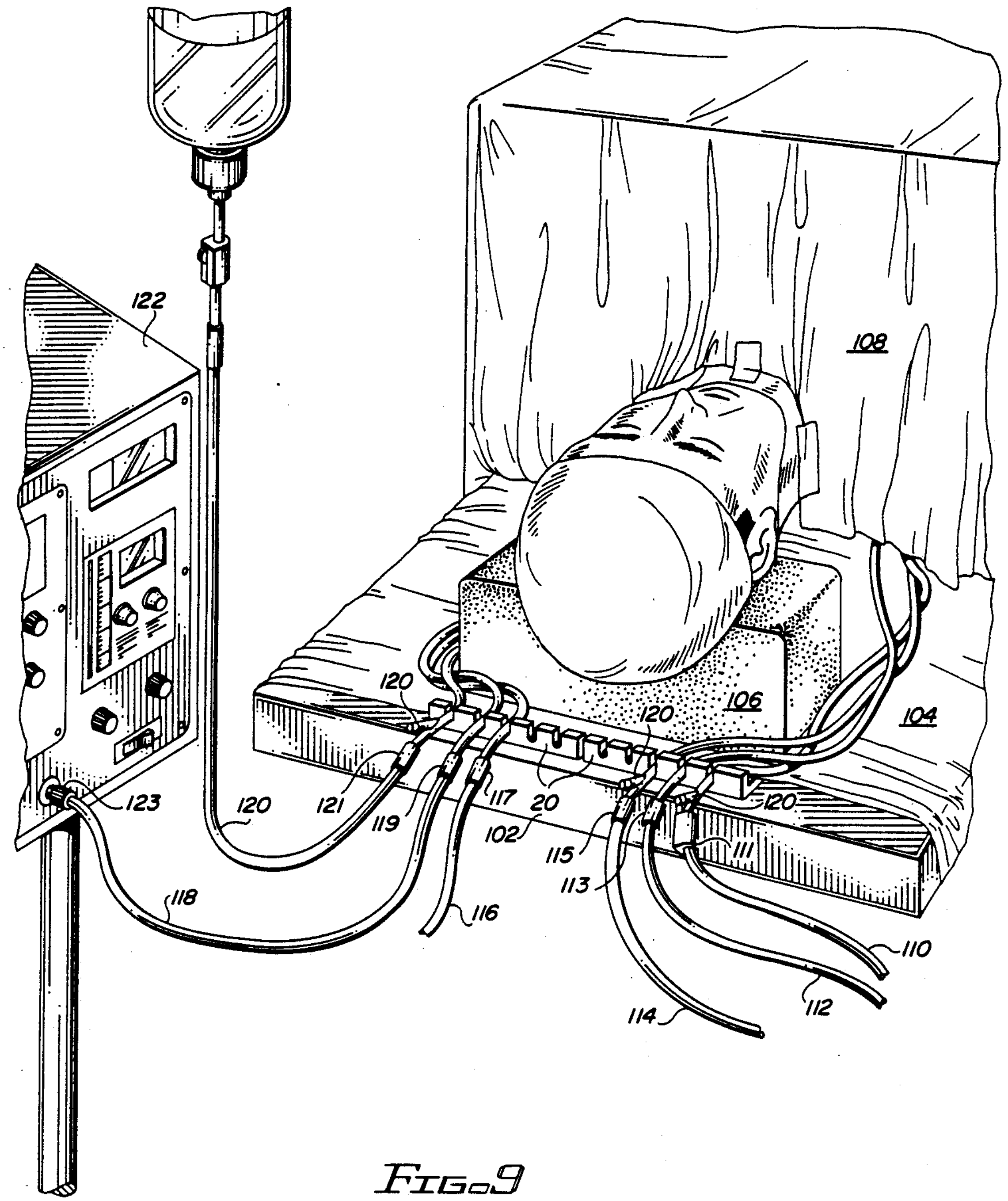
FIG. 9 is a perspective view illustrating the manner of use of the present invention during a surgical procedure.

In FIG. 7, a one-way valve assembly 80 is positioned in a groove 60 of the manifold 20 of FIG. 6. The assembly 80 includes a valve 81, an injection port 82, a luer lock 83, and a friction locking member 84 which locks the valve assembly 80 into the groove 60. An inlet IV line 85 feeds into the valve 81, and an outlet IV line 86 is connected to the patient. An IV flow-regulating clamp 87 is typically used along the inlet side of the IV line. Identification sleeves 88 and 89, which are described more fully below with respect to FIGS. 9 and 10, are also employed. In the arrangement of FIG. 7, the valve assembly 80 is constructed so that the injection port 82 faces upwardly, thus permitting easy access during use. It will be noted that the specific features of the assembly in FIG. 7 also provide for the valve 81 and port 82 to be located on the physician's side of the manifold 20.

In the embodiment of FIG. 8, the distal end 18 of the wing 14 includes a keyway 94 adapted to receive a mating key 92 on a disposable manifold plate 90. In FIG. 8, there is provided a vertical groove 96 having a locking slot 98 extending outwardly from the groove 96, with the slot 98 adapted to receive a locking tab 99 associated with a disposable one way valve assembly 74, like that described above.

When the apparatus 10 is in use, the patient is placed upon the upper surface of the pad 48 so as to be supported by the member 22, with the patient's head toward the upper end 24 and the patient's feet extending beyond the lower end 26. As dictated by the requirements of the patient's status (i.e., in transport, pre-op, post-op, etc.), the wings 12, 14 may be positioned in any desired location between the two extreme positions depicted in FIG. 1, and the various catheters, intravenous and monitoring lines and the like placed at the conventional entry sites into the patient's body, for example, in the arm, chest or neck of the patient. It, of course, may be desirable to provide a certain degree of slack between the respective manifold 20 and the entry site into the patient's body for a particular catheter or line.

While the patient is in the operating room, it will usually be preferred to have rotated the wings 12, 14 into the second extreme position (note FIG. 4). In this position, the conventional sterile field drapes may be placed over the patient's body while permitting the anesthesiologist to monitor the various medication, intravenous and other fluid and monitoring lines and injection ports at the manifolds 20 which will then be located above the patient's head. At the same time, the various catheters and lines are rotated away from the patient's side, and out of the way of the surgical team. Thus, the wings and manifolds create a fixed, rotatable location at which all of the intravenous, catheter and pressure monitoring lines are organized, so that those lines and catheters may be easily and quickly identified in a facile manner. Once the catheters and lines are properly identified, the organization and identification of those plural catheters and lines will remain intact.

FIG. 9 depicts the view during surgical procedures typically seen by an anesthesiologist, in which the patient is placed upon an operating table 102 with a sheet 104 across the surface of the operating table, and with a head rest 106 supporting the patient's head. A drape 108 is used to establish a sterile field around the surgical site, thus prohibiting the anesthesiologist from having a complete view of the patient (and the entry sites for the various catheters, monitoring lines and intravenous lines) during the operation. In the past, those catheters, intravenous and monitoring lines were typically taped to the sheet 104. However, when employing the apparatus of the present invention and the associated method, the manifolds 20 are extended into the second extreme position, as depicted in FIG. 9, so as to receive the various catheters, intravenous lines and pressure monitoring lines 110, 112, 114, 116 and 118. Additionally, the manifolds 20 are designed to receive, organize and maintain medicine injection ports of the type depicted as element 120 in FIG. 9. It will also be understood that one way valves like that described above with reference to FIGS. 6–8 may also be used during the surgical procedure.

In accordance with another aspect of the present invention, the identity of each catheter, intravenous line or monitoring line is further facilitated by the use of an identification sleeve on each line, such as sleeves 111, 113, 115, 117, 119 and 121 which are respectively associated with catheters and lines 110, 112, 114, 116 and 118. The injection port 120 may also have an associated identification sleeve 121 next adjacent to the port. It will be understood that each of the catheters, intravenous lines and pressure monitoring lines used in any surgical procedure are connected to some type of operating room equipment, such as (for example) a medication metering system 122 depicted in FIG. 9. The catheter 118 associated with the metering machine 122 has an identification sleeve 123 at the end thereof which enters the machine 122, and which sleeve 123 corresponds in color, identification symbol or the like to sleeve 119 in order to permit the anesthesiologist to rapidly and properly correlate and identify the catheter at manifold 20 with the associated medication metering machine 122. It will, of course, be understood that each of the catheters, intravenous lines and pressure monitoring lines 110, 112, 114, 116 and 118 likewise have associated identification sleeves at the other end thereof, or near an associated flow regulating clamp, if appropriate.

As shown in FIG. 10, each identification sleeve, such as sleeve 121 may simply comprise a plastic tube having a longitudinal slit 124 which permits the identification sleeve to be easily slipped over and frictionally engaged on the respective end of the associated catheter.

It will thus be understood that the present invention is a portable and light weight apparatus which permits the various catheters and other lines entering the patient's body to be easily and quickly organized, identified and maintained, even during emergency conditions.

It will also be understood by those skilled in the art that various modifications may be made in the apparatus and method described above without departing from the spirit and scope of the present invention. For example, where it is not required for the support member to be fluoroscopically transparent, then a metal sheet, such as aluminium, may be suitable. Further, the support member may be made to extend the full length of the patient's body, and additional rotatable wings may be affixed at the foot end of the support member to organize, identify and maintain any additional catheters that may be used for insertion into the lower portion of the patient's body.

What is claimed is:

1. A system for organizing, identifying and maintaining a plurality of tubes, catheters, monitoring lines or intravenous lines entering a patient's body during a medical procedure, comprising:

a patient support;

plural medical treatment apparatus at spaced locations near said patient support;

plural tubes, catheters, monitoring lines or intravenous lines, each extending at one, distal end from one of said treatment apparatus and interconnected with the patient's body;

a manifold movably coupled with the support, the manifold having plural openings, each opening receiving one of said tubes, catheters, monitoring lines or intravenous lines and holding all of them in an organized, spaced relation; and coding means at the manifold and at the distal ends for identifying each tube, catheter, monitoring line or intravenous line with the corresponding one of said medical treatment apparatus.

2. The system recited in claim 1 wherein said patient support has a first end dimensioned to receive the patient's head during the medical procedure; and further comprising means for supporting said manifold adjacent said first end.

3. The system recited in claim 1 wherein said coding means comprises a valve assembly held in one of said manifold opening sand specifically associated with one of said medical treatment apparatus.

4. The system recited in claim 1 wherein said coding means comprises corresponding color-coding on each tube, catheter, monitoring line or intravenous lines at both the distal end thereof and at said manifold.

5. The system recited in claim 45, further comprising a member positioned on the patient support, said member having at least one wing movable relative to said member, said manifold joined with the wing in a relatively fixed relation during movement of said wing; said member being defined by first and second opposing ends and first and second opposing sides extending between said ends, said member adapted to receive the patient's head at said first end and with the patient's torso extending along said member generally parallel with a portion of said sides; said wing being rotatable through an arc into numerous positions between a first position generally lateral to one of said sides and a second position generally parallel to said sides; and wherein said wing extends beyond said first end in said second position.

6. The apparatus recited in claim 1 wherein said wing lies in, and is movable in a plane which is generally parallel to the plane of said surface upon which the patient rests.

7. The apparatus recited in claim 1 wherein said receiving means comprises catheter engaging means near the distal extremity of said wing, said engaging means extending generally lateral from the plane of said wing.

8. The apparatus recited in claim 1 wherein said wing extends beyond one of said sides in said first position.

9. The apparatus recited in claim 1 further comprising means for preventing rotation of said wing beyond said first position in a direction toward said second end.

10. The apparatus recited in claim 1 wherein the dimension between said first and second sides defines a first, narrow neck portion of said member adjacent said first end and a wider body portion of said member from about the point of rotation of said wing toward said second end.

11. The apparatus recited in claim 10 wherein said first and second wings extend alongside said narrow neck portion when in said second position.

12. The apparatus recited in claim 1 wherein said wing has a friction against rotation.

13. The system recited in claim 45, further comprising a member defining at least one wing, said wing having said manifold fixed thereto, said manifold further including means positively locking each catheter, tube, monitoring line or intravenous line in the corresponding opening of said manifold.

14. The system recited in claim 45, further comprising a member positioned on the patient support and having a first surface dimensioned to receive a patient thereon, said member defining at least one rotatable wing extending away from said patient support, said wing having said manifold fixed thereto during movement of said wing; and wherein said member further comprises a second surface opposing said first surface, said wing rotatably coupled to said member along said second surface.

15. The apparatus recited in claim 14 further comprising a plate member attached to said member along said second surface for preventing rotation of said wing beyond a first position which is generally lateral to one of said sides.

16. The system recited in claim 16, wherein said member is portable, further comprising a carrying handle along said member for permitting the lifting of said member while the patient is resting thereon.

17. The system recited in claim 45, further comprising:

a portable member placed upon said patient support, said member having an upper patient support surface;

a pair of wings, each wing having a distal end extending away from said member, and a proximal end rotatably coupled with said member so that each wing rotates in a plane which is generally parallel with said patient's support surface; and two manifolds, each manifold fixed to a wing and receiving and holding plural tubes, catheters, monitoring lines or intravenous lines in fixed relation to the patient during rotation of the corresponding wing.

18. The apparatus recited in claim 17 wherein said member is defined by first and second opposing ends and first and second opposing sides extending between said ends, said member adapted to receive the patient's head at said first end and with the patient's torso extending along said member generally parallel with a portion of said side and wherein said wings are rotatable through an arc into numerous positions between a first position generally lateral to a corresponding side and a second position generally parallel to the corresponding side.

19. The apparatus recited in claim 18 wherein said wings extend beyond said first end in said second position.

20. The apparatus recited in claim 18 wherein the dimension between said first and second sides defines a first head portion of said member adjacent said first end and a wider body portion of said member toward said second end.

21. The system recited in claim 45, further comprising a wing extending across said patient support, and a pair of manifolds, one of the manifolds attached at the distal end of said wing, each manifold having plural slots each for fixing and maintaining a plurality of said tubes, catheters, monitoring lines or intravenous lines in an organized, spaced relation independent of the tubes, catheters, monitoring lines or intravenous lines fixed and maintained in the other manifold.

22. The apparatus recited in claim 21 further comprising means at said proximal end for rotating said wing while maintaining said tubes and catheters in said fixed, spaced relation.

23. The system recited in claim 21, further comprising means for removing said manifold from said wing by sliding said manifold relative to said wing.

24. The system recited in claim 45, wherein the coding means comprises a removable identifying sleeve at each distal end of each tube, catheter, monitoring line or intravenous line, and a corresponding removable identification sleeve on each catheter or the like adjacent said manifold.

25. Apparatus for organizing and maintaining a plurality of catheters, tubes, monitoring lines or intravenous lines for a patient resting upon an operating table or similar patient support and undergoing medical care, said apparatus comprising:

an operating table;

plural medical treatment apparatus at space locations near said operating table;

plural catheters, tubes, monitoring lines and intravenous lines, each extending at one, distal end from one of the treatment apparatus and interconnected with the patient's body;

a support member positioned at the end of the operating table adjacent the patient's head, the support member having a surface;

a manifold removably coupled with said support member surface, the manifold comprising an upstanding flat plate extending generally parallel with the end of the operations table and having plural slots interconnecting with said catheters, tubes, monitoring lines and intravenous lines connected to the patient;

means for removing the manifold with a movement of the plate along the surface; and coding means at the manifold and at the distal ends for identifying each catheter, tube, monitoring line or intravenous line with the corresponding one of the medical treatment apparatus.

26. Apparatus for organizing and maintaining a plurality of catheters, tubes, monitoring lines and intravenous lines used during and after the care of a patient in a surgical procedure comprising:

a surgical table for supporting a patient;

plural medical treatment apparatus at space locations near said surgical table;

plural catheters, tubes, monitoring lines and intravenous lines, each extending at one distal end from one of the treatment apparatus and interconnected with the patient's body;

a wing member extending at one end under the patient's head on the surgical table;

a manifold having plural spaced slots therein coupling the catheters, tubes, monitoring lines and intravenous lines to the manifold so that the catheters, tubes, monitoring lines and intravenous lines are maintained in a fixed and organized relationship;

means for removably attaching the manifold at the other end of the wing member, and for maintaining the fixed and organized relationship of catheters, tubes, monitoring lines and intravenous lines in the manifold after removal;

coding means at the manifold and at the distal ends for identifying each catheter tube, monitoring line or intravenous line with the corresponding one at the medical treatment apparatus;

means for retaining a catheter, tube, monitoring line or intravenous line in each slot; and wherein the manifold may be removed from the other end of the wing member and thereafter placed with the patient during movement of the patient out of the surgical area, while maintaining the fixed relationship of the catheters, monitoring lines or intravenous lines fixed in the manifold.

27. The apparatus recited in claim 26 wherein the removable attaching means comprises means for attaching the manifold to the wing member by a sliding movement of the manifold with respect to the wing member.

28. The apparatus recited in claim 27 wherein the sliding movement attaching means comprises a keyway in the other end of the wing member and a key in the manifold.

29. The apparatus recited in claim 26 wherein the retaining means comprises a locking tab fitted about each catheter, monitoring line or intravenous line.

30. The apparatus recited in claim 26 further comprising an identifying sleeve at one end of each catheter, monitoring line or intravenous line at the manifold, and a corresponding identification sleeve on each catheter, monitoring line or intravenous line at the other end of such catheter, monitoring line or intravenous line.

* * * * *

UNITED STATES PATENT AND TRADEMARK OFFICE

CERTIFICATE OF CORRECTION

PATENT NO. : 4,988,062

DATED : January 29, 1991

INVENTOR(S) : Robert A. London

It is certified that error appears in the above-identified patent and that said Letters Patent is hereby corrected as shown below:

Col. 9, line 13 (Claim 24): "Claim 45" should be --Claim 1--.

Signed and Sealed this

Twenty-sixth Day of May, 1992

*Attest:*

DOUGLAS B. COMER

*Attesting Officer*

*Acting Commissioner of Patents and Trademarks*